(12) United States Patent
Dykema et al.

(10) Patent No.: US 10,888,436 B2
(45) Date of Patent: Jan. 12, 2021

(54) TIBIAL TRAY IMPACTOR

(71) Applicant: Zimmer, Inc., Warsaw, IN (US)

(72) Inventors: Scott Dykema, Warsaw, IN (US); Brian Edward Roach, Osceola, IN (US)

(73) Assignee: Zimmer, Inc., Warsaw, IN (US)

( * ) Notice: Subject to any disclaimer, the term of this patent is extended or adjusted under 35 U.S.C. 154(b) by 286 days.

(21) Appl. No.: 15/880,975

(22) Filed: Jan. 26, 2018

(65) Prior Publication Data
US 2018/0214281 A1 Aug. 2, 2018

Related U.S. Application Data

(60) Provisional application No. 62/453,177, filed on Feb. 1, 2017.

(51) Int. Cl.
*A61F 2/46* (2006.01)
*A61F 2/38* (2006.01)
*A61B 17/92* (2006.01)

(52) U.S. Cl.
CPC .............. *A61F 2/461* (2013.01); *A61B 17/92* (2013.01); *A61F 2/389* (2013.01); *A61F 2/4603* (2013.01); *A61F 2002/4628* (2013.01); *A61F 2002/4681* (2013.01)

(58) Field of Classification Search
CPC ..................... A61F 2/461; A61F 2/4603; A61F 2002/4628; A61B 17/92; A61B 2017/922; A61B 2017/924
See application file for complete search history.

(56) References Cited

U.S. PATENT DOCUMENTS

| 4,364,389 A | 12/1982 | Keller |
| 4,889,022 A | 12/1989 | Peviani |
| 4,919,679 A | 4/1990 | Averill |
| 5,059,196 A | 10/1991 | Coates |
| 5,064,427 A | 11/1991 | Burkinshaw |

(Continued)

FOREIGN PATENT DOCUMENTS

| CN | 110234288 A | 9/2019 |
| EP | 2777636 | 9/2014 |

(Continued)

OTHER PUBLICATIONS

"International Application Serial No. PCT US2018 015405, International Search Report dated Aug. 29, 2018", 4 pgs.

(Continued)

*Primary Examiner* — Matthew J Lawson
(74) *Attorney, Agent, or Firm* — Schwegman Lundberg & Woessner, P.A.

(57) ABSTRACT

An impactor tool can include a handle, an impactor, a lock, an actuator, and a pin. The impactor can be coupled to the handle. The lock can be extendable from the impactor to engage an implant and retractable into the impactor to secure the lock and the impactor to the implant. The actuator can protrude from the impactor and can be coupled to the lock. The actuator can include a cam defined by a channel extending through the actuator. The pin can be coupled to the lock and disposed within the cam channel, where the actuator can be operable along a path defined by the cam and the pin to extend and retract the lock.

17 Claims, 9 Drawing Sheets

(56) References Cited

U.S. PATENT DOCUMENTS

| | | | |
|---|---|---|---|
| 5,333,773 | A | 8/1994 | Main et al. |
| 5,356,414 | A | 10/1994 | Cohen et al. |
| 5,409,492 | A | 4/1995 | Jones et al. |
| 5,514,136 | A | 5/1996 | Richelsoph |
| 5,733,292 | A | 3/1998 | Gustilo et al. |
| 5,788,701 | A | 8/1998 | Mccue |
| 5,849,015 | A | 12/1998 | Haywood et al. |
| 6,113,605 | A | 9/2000 | Storer |
| 6,783,551 | B1 | 8/2004 | Metzger et al. |
| 7,048,742 | B2 | 5/2006 | Keller |
| 7,338,497 | B2 | 3/2008 | Coon et al. |
| 7,776,044 | B2 | 8/2010 | Pendleton et al. |
| 8,435,241 | B2 | 5/2013 | Correia et al. |
| 8,758,360 | B2 | 6/2014 | Green, II |
| 8,870,886 | B2 | 10/2014 | Burgi |
| 8,986,390 | B2 | 3/2015 | Wogoman et al. |
| 9,095,356 | B2 | 8/2015 | Thomas et al. |
| 9,107,757 | B2 | 8/2015 | Major et al. |
| 9,220,611 | B2 | 12/2015 | Jones et al. |
| 9,901,462 | B2 | 2/2018 | Jones et al. |
| 2001/0034554 | A1 | 10/2001 | Pappas |
| 2002/0092871 | A1 | 7/2002 | Rickard et al. |
| 2004/0010261 | A1 | 1/2004 | Hoag et al. |
| 2005/0124998 | A1 | 6/2005 | Coon et al. |
| 2006/0095043 | A1 | 5/2006 | Martz et al. |
| 2006/0136067 | A1 | 6/2006 | Pendleton et al. |
| 2006/0200162 | A1* | 9/2006 | Farling ............... A61F 2/461 606/88 |
| 2007/0167952 | A1 | 7/2007 | Burgi et al. |
| 2008/0119941 | A1 | 5/2008 | Seo et al. |
| 2008/0172061 | A1* | 7/2008 | Ragbir ............... A61F 2/4612 606/99 |
| 2009/0036909 | A1 | 2/2009 | Perry et al. |
| 2011/0186456 | A1 | 8/2011 | Bertazzoni et al. |
| 2012/0143204 | A1* | 6/2012 | Blaylock ............ A61F 2/3859 606/99 |
| 2013/0018382 | A1 | 1/2013 | Jones et al. |
| 2014/0094812 | A1 | 4/2014 | Edwards et al. |
| 2014/0277541 | A1 | 9/2014 | Wys et al. |
| 2015/0045800 | A1 | 2/2015 | Berelsman et al. |
| 2015/0342742 | A1 | 12/2015 | Ferro et al. |
| 2016/0067057 | A1 | 3/2016 | Jones et al. |

FOREIGN PATENT DOCUMENTS

| | | |
|---|---|---|
| EP | 2837364 | 2/2015 |
| GB | 2307861 A | 6/1997 |
| WO | 2018144332 | 8/2018 |

OTHER PUBLICATIONS

"International Application Serial No. PCT US2018 015405, Written Opinion dated Aug. 29, 2018", 7 pgs.

"U.S. Appl. No. 14/943,280, PTO Response to Rule 312 Communication dated Jan. 29, 2018", 2 pgs.

"U.S. Appl. No. 13/181,070, Advisory Action dated Sep. 25, 2014", 2 pgs.

"U.S. Appl. No. 13/181,070, Examiner Interview Summary dated Jun. 17, 2015", 3 pgs.

"U.S. Appl. No. 13/181,070, Final Office Action dated Jun. 26, 2014", 18 pgs.

"U.S. Appl. No. 13/181,070, Non Final Office Action dated Apr. 20, 2015", 16 pgs.

"U.S. Appl. No. 13/181,070, Non Final Office Action dated Nov. 26, 2013", 19 pgs.

"U.S. Appl. No. 13/181,070, Notice of Allowance dated Aug. 21, 2015", 5 pgs.

"U.S. Appl. No. 13/181,070, Response filed May 27, 2014 to Non-Final Office Action dated Nov. 26, 2013", 18 pgs.

"U.S. Appl. No. 13/181,070, Response filed Jul. 17, 2015 to Non Final Office Action dated Apr. 20, 2015", 14 pgs.

"U.S. Appl. No. 13/181,070, Response filed Sep. 19, 2014 to Final Office Action dated Jun. 26, 2014", 16 pgs.

"U.S. Appl. No. 13/181,070, Response filed Oct. 22, 2013 to Restriction Requirement dated Sep. 23, 2013", 13 pgs.

"U.S. Appl. No. 13/181,070, Restriction Requirement dated Sep. 23, 2013", 5 pgs.

"U.S. Appl. No. 14/943,280, Advisory Action dated Jun. 7, 2017", 3 pgs.

"U.S. Appl. No. 14/943,280, Examiner Interview Summary dated Apr. 11, 2017", 2.

"U.S. Appl. No. 14/943,280, Final Office Action dated Jan. 18, 2017", 6 pgs.

"U.S. Appl. No. 14/943,280, Non Final Office Action dated Apr. 1, 2016", 13 pgs.

"U.S. Appl. No. 14/943,280, Non Final Office Action dated Aug. 11, 2016", 14 pgs.

"U.S. Appl. No. 14/943,280, Notice of Allowance dated Oct. 18, 2017", 5 pgs.

"U.S. Appl. No. 14/943,280, Preliminary Amendment filed Nov. 18, 2015", 6 pgs.

"U.S. Appl. No. 14/943,280, Response filed Apr. 18, 2017 to Final Office Action dated Jan. 18, 2017", 12 pgs.

"U.S. Appl. No. 14/943,280, Response filed Jun. 29, 2016 to Non Final Office Action dated Apr. 1, 2016", 11 pgs.

"U.S. Appl. No. 14/943,280, Response filed Dec. 12, 2016 to Non Final Office Action dated Aug. 11, 2016", 11 pgs.

"U.S. Appl. No. 14/943,280, Supplemental Preliminary Amendment filed Dec. 2, 2015", 6 pgs.

"Journey BCS total knee replacement Part 2, Dr. Venkatachalam, accessed Dec. 15, 2010 and May 28, 2012", This link shows the use of surgical instruments (0:30 starts use of a provisional extractor, 4:00 starts use of an implant inserter), [Online]. Retrieved from the Internet: <http://www.youtube.com/watch?v=zWPlkUbMfZI>on Dec. 16, 2013, (Sep. 21, 2010), 2 pgs.

"Oxinium Knee Replacement—Venkatachalam Part 1, accessed Dec. 15, 2010 and May 28, 2012", This link shows the use of a trial impactor/extractor (starting at 5:15 and continued on the below link), [Online]. Retrieved from the Internet: <http://www.youtube.com/watch?v=J-KFQDB6Tb4&feature=related> on Dec. 16, 2013, (Jul. 27, 2010), 2 pgs.

"Smith & Nephew Journey BCS Bi-Cruciate Stabilized Knee System Surgical Technique", Smith & Nephew, Inc. Sep. 2007, 1-60, Sep. 2007.

"Zimmer MIS Intramedullary Instrumentation Surgical Technique for NexGen Cruciate Retaining & NexGen Legacy Posterior Stabilized Knees", printed 2005, 2009, Zimmer, Inc., (2009), 45 pgs.

"European Application Serial No. 18707453.9, Response to Communication pursuant to Rules 161(1) and 162 EPC, filed Apr. 6, 2020", 80 pgs.

\* cited by examiner

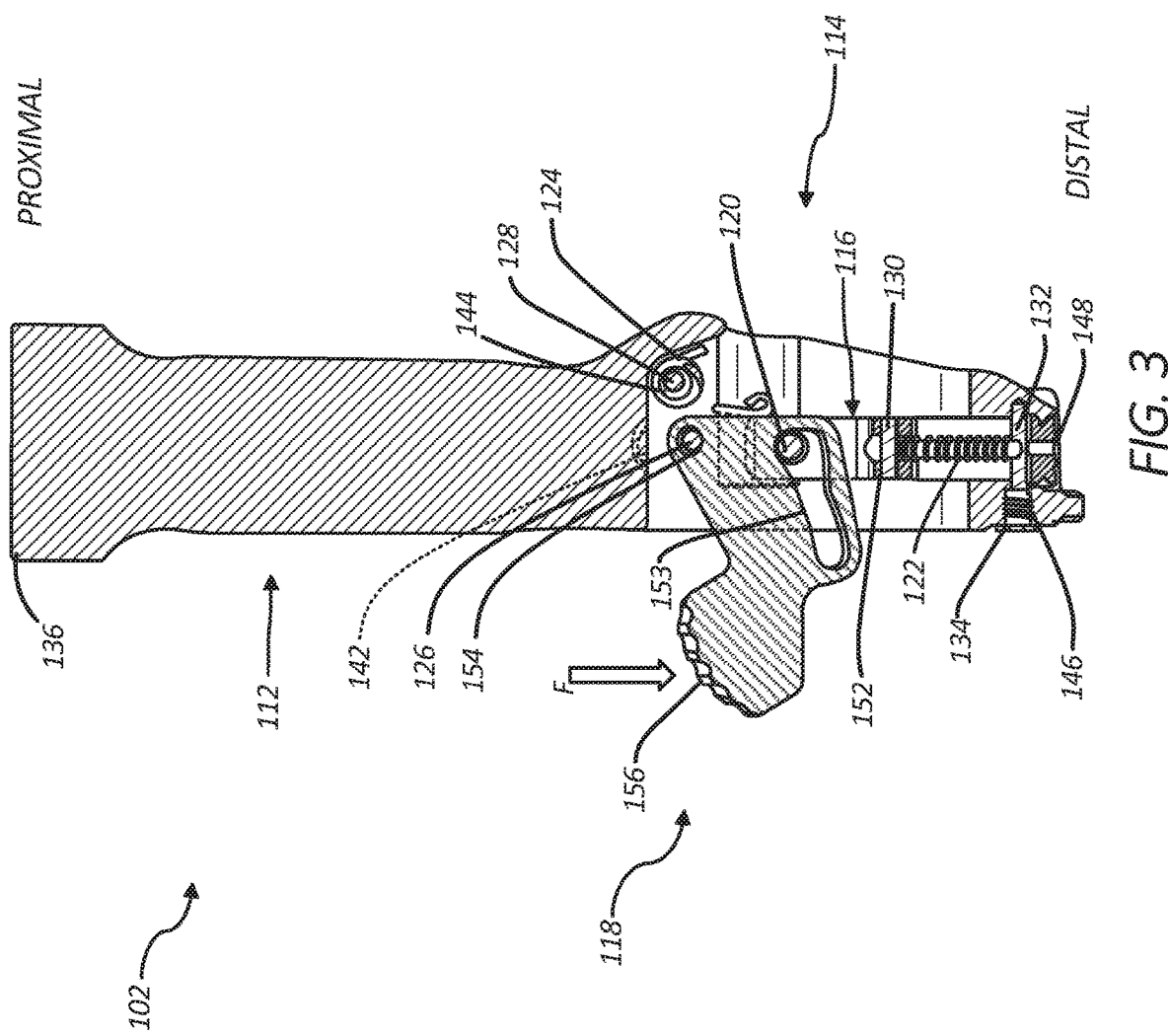

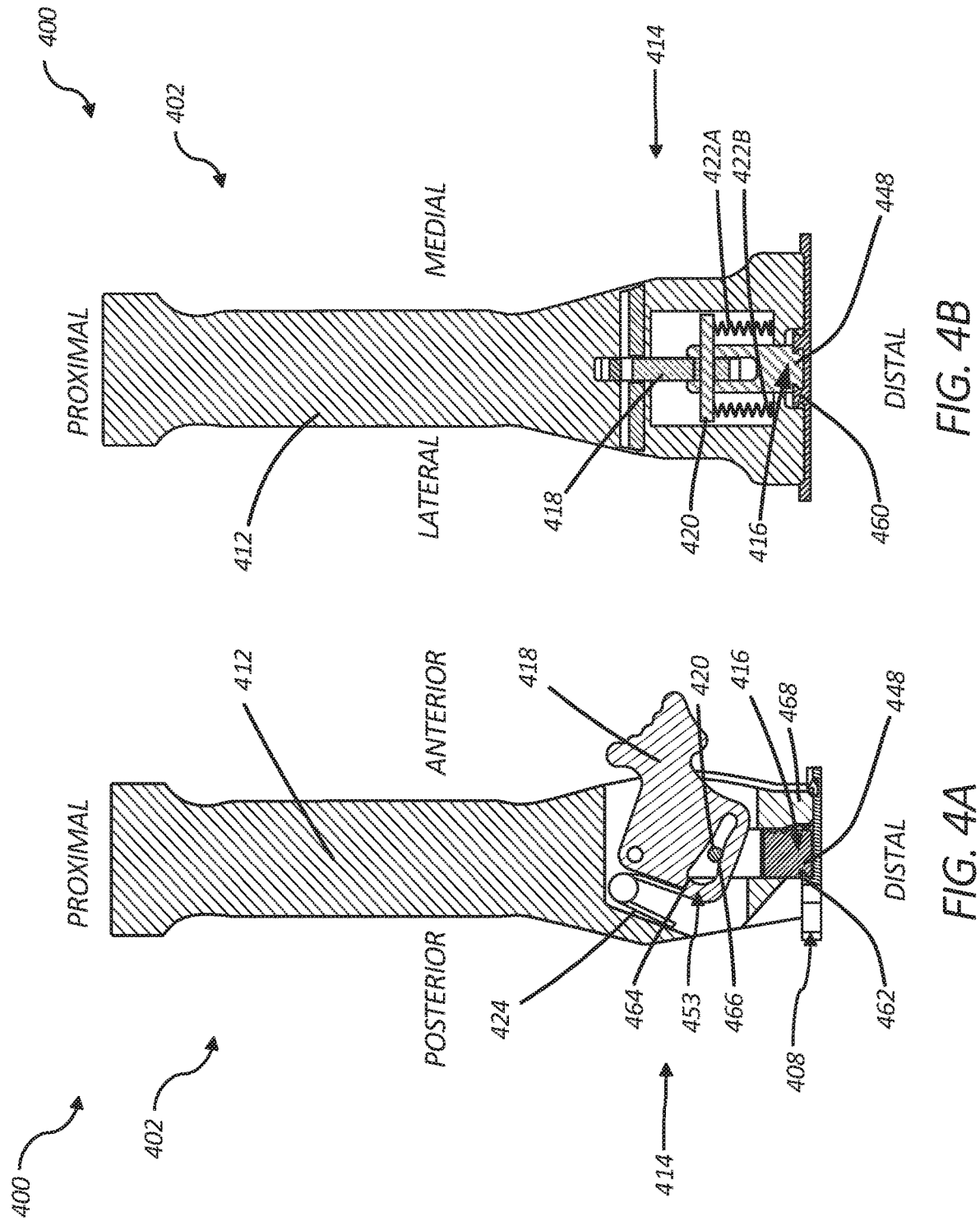

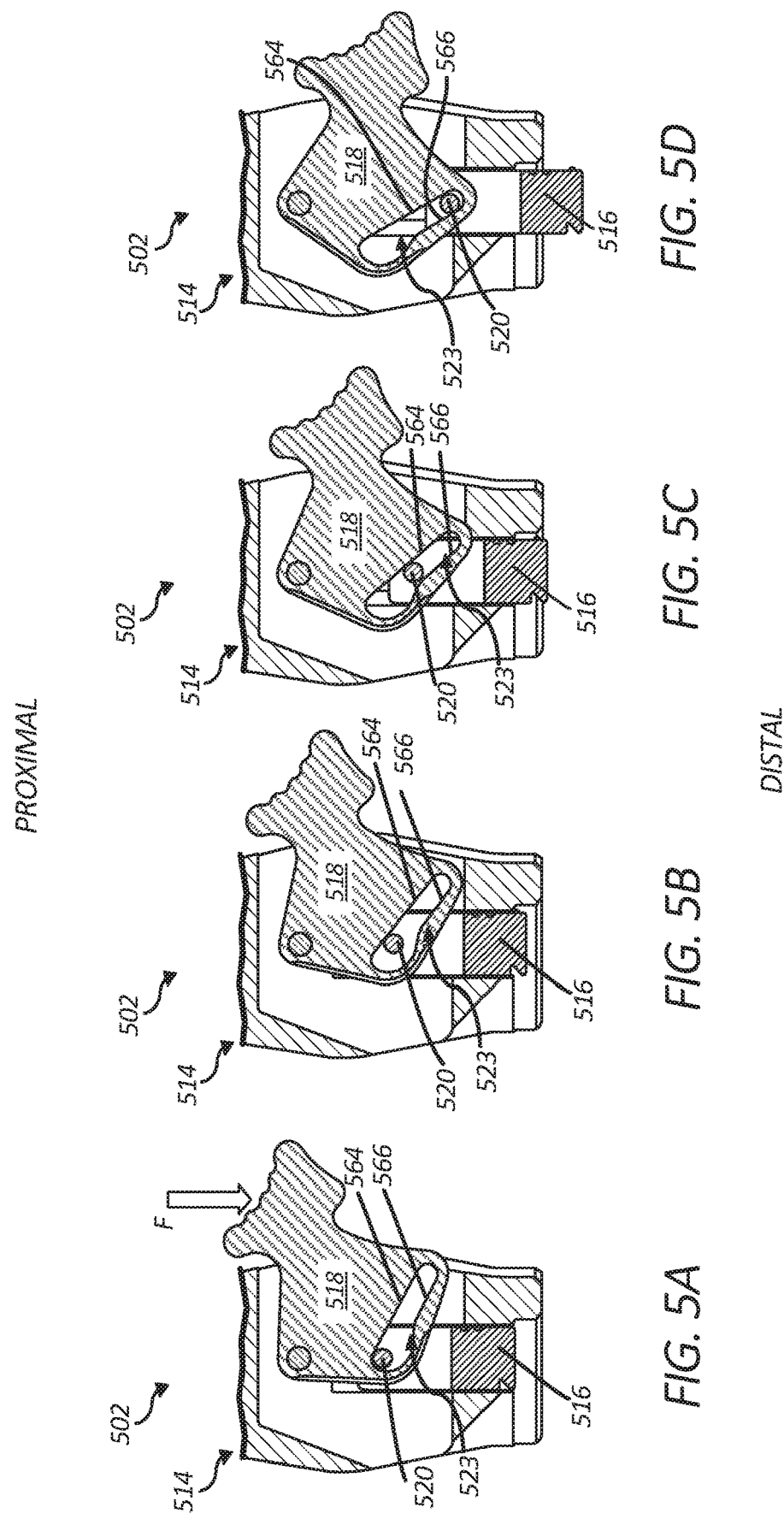

TIBIAL TRAY IMPACTOR

CLAIM OF PRIORITY

This application claims the benefit of priority to U.S. Provisional Application Ser. No. 62/453,177, filed on Feb. 1, 2017, which is incorporated herein by reference in its entirety.

FIELD

The present subject matter relates to orthopedic prostheses and, more particularly, to knee joint arthroplasties.

BACKGROUND

Orthopedic procedures and prostheses are commonly utilized to repair and/or replace damaged bone and tissue in the human body. For example, a knee arthroplasty can be used to restore natural knee function by repairing damaged or diseased articular surfaces of the femur and/or tibia. An incision is made into the knee joint to expose the bones comprising the joint. Cut guides are used to guide the removal of the articular surfaces that are to be replaced. Prostheses are used to replicate the articular surfaces. Knee prostheses can include a femoral component implanted on the distal end of the femur, which articulates with a tibial bearing component and a tibial component implanted on the proximal end of a tibia to replicate the function of a healthy natural knee. Various types of arthroplasties are known including a total knee arthroplasty, where all of the articulating compartments of the joint are repaired with prosthetic components.

OVERVIEW

This disclosure pertains generally to tibial prostheses, systems, and methods for a knee arthroplasty and/or as part of a knee revision surgery. The present inventors have recognized, among other things, that tibial trays may require a substantial force to be inserted into the tibia of a patient. Accordingly, special tools may be required to aid insertion, such as an impactor and an impacting device. In such cases, the impactor used to drive the tibial tray into the tibia may be susceptible to slipping off the tibial tray due to an impact from an impacting tool, such as a hammer or mallet. This can result in damage to the impactor, tibial tray, and in some cases, can cause harm to a patient. In previous examples, impactors have been designed to be secured or locked to a tibial tray. However, some of these impactors are difficult or slow to operate, or may be accidentally disengaged. Some other impactors are very heavy and others are complex and therefore expensive. Thus, the present inventors propose an impactor tool including an elongate handle coupled to an impactor. The impactor can include an extending and retracting locking mechanism that is operated by an actuator including a cam. A pin of the impactor tool is movable within the cam to convert movement of the actuator to translation of the lock. A compression spring can be included to bias the lock to a retracted position and a torsion spring can be included to bias the actuator to an outward position. The impactor tool design offers a lightweight impactor tool that is simple and fast to operate. Also, due to the relative simplicity of the design (few moving components), the impactor can be of a lower relative cost.

To further illustrate the apparatuses and systems disclosed herein, the following non-limiting examples are provided:

Example 1 is an impactor tool comprising: a handle; an impactor coupled to the handle; a lock extendable from the impactor to engage an implant and retractable into the impactor to secure the lock and the impactor to the implant; an actuator protruding from the impactor and coupled to the lock, the actuator comprising: a cam defined by a channel extending through the actuator; and a pin coupled to the lock and disposed within the cam channel, the actuator operable along a path defined by the cam and the pin to extend and retract the lock.

In Example 2, the subject matter of Example 1 optionally includes a compression member in contact with the lock and the impactor, the compression member biasing the lock to retract into the impactor.

In Example 3, the subject matter of Example 2 optionally includes the actuator further comprising: a lever operable to rotate the actuator.

In Example 4, the subject matter of Example 3 optionally includes the cam channel defined by: a ramp side surface biased by the compression member to engage the pin when the actuator is operated to extend the lock from the impactor.

In Example 5, the subject matter of Example 4 optionally includes a torsion member internally coupled to the impactor and engageable with an internal portion of the actuator to bias the actuator to an outward position.

In Example 6, the subject matter of Example 5 optionally includes the cam channel further defined by: a cam side surface opposite the ramp side surface, the cam side surface biased by the torsion member to engage the pin when the actuator is released and when the lock and impactor are secured to the implant.

In Example 7, the subject matter of Example 6 optionally includes the cam side further comprising: a continually variable radiused surface in the cam side surface and curved away from the ramp side surface, the continually variable radiused surface engageable with the pin to restrict the lever from moving inward when the lock and the impactor are secured to the implant.

In Example 8, the subject matter of any one or more of Examples 1-7 optionally include a pivot pin connected to the impactor and extending through the actuator, the actuator rotatable about the pivot pin.

In Example 9, the subject matter of any one or more of Examples 1-8 optionally include a mating feature disposed proximate a distal termination of the lock, the mating feature engageable with the implant.

Example 10 is a tibial implant impactor assembly comprising: a tibial tray mateable with a resected portion of a tibia; an implant impactor tool comprising: a handle; an impactor connected to the handle and engageable with the tibial implant; and a lock extendable from the impactor to engage an implant and retractable into the impactor to secure the lock and the impactor to the tibial tray; an actuator protruding from the impactor and coupled to the lock, the actuator comprising: a cam defined by a channel extending through the actuator; and a pin coupled to the lock and disposed within the cam channel, the actuator operable along a path defined by the cam and the pin to extend and retract the lock.

In Example 11, the subject matter of Example 10 optionally includes a mating feature disposed proximate a distal termination of the lock, the mating feature engageable with the implant.

In Example 12, the subject matter of Example 11 optionally includes the tibial tray further comprising: a slot engageable with the mating feature to secure the tool to the tibial tray.

In Example 13, the subject matter of any one or more of Examples 10-12 optionally include a compression member in contact with the lock and the impactor, the compression member biasing the lock to retract into the impactor.

In Example 14, the subject matter of Example 13 optionally includes a torsion member internally coupled to the impactor and engageable with an internal portion of the actuator to bias the actuator to an outward position.

In Example 15, the subject matter of Example 14 optionally includes the cam defined by: a ramp side surface biased by the compression member to engage the pin when the actuator is operated to extend the lock from the impactor.

In Example 16, the subject matter of Example 15 optionally includes the cam further defined by: a cam side surface opposite the ramp side surface, the cam side surface biased by the torsion member to engage the pin when the actuator is released and when the lock and impactor are secured to the implant.

In Example 17, the subject matter of Example 16 optionally includes a continually variable radiused surface in the cam side surface and curved away from the ramp side surface, the continually variable radiused surface engageable with the pin to restrict the lever from moving inward when the lock and the impactor are secured to the implant.

Example 18 is a method of inserting a tibial implant, the method comprising: operating an actuator to extend a lock from an impactor of a tibial impactor tool; engaging an implant with the lock; releasing the actuator to retract the lock and causing the impactor to contact the implant.

In Example 19, the subject matter of Example 18 optionally includes impacting the tibial impactor tool with an impacting device.

In Example 20, the subject matter of any one or more of Examples 18-19 optionally include wherein operating the actuator moves a pin that controlled by a cam defined by the actuator, and wherein the pin is coupled to the lock.

In Example 16, the subject matter of Example 15 optionally includes the cam further defined by: a cam side surface opposite the ramp side surface, the cam side surface biased by the torsion member to engage the pin when the actuator is released and when the lock and impactor are secured to the implant.

In Example 17, the subject matter of Example 16 optionally includes a continually variable radiused surface in the cam side surface and curved away from the ramp side surface, the continually variable radiused surface engageable with the pin to restrict the lever from moving inward when the lock and the impactor are secured to the implant.

Example 18 is a method of inserting a tibial implant, the method comprising: operating an actuator to extend a lock from an impactor of a tibial impactor tool; engaging an implant with the lock; releasing the actuator to retract the lock and causing the impactor to contact the implant.

In Example 19, the subject matter of Example 18 optionally includes impacting the tibial impactor tool with an impacting device.

In Example 20, the subject matter of any one or more of Examples 18-19 optionally include wherein operating the actuator moves a pin that controlled by a cam defined by the actuator, and wherein the pin is coupled to the lock.

Example 21 is an impactor tool comprising: a handle; an impactor coupled to the handle; a lock extendable from the impactor to engage an implant and retractable into the impactor to secure the lock and the impactor to the implant; an actuator protruding from the impactor and coupled to the lock, the actuator comprising: a cam defined by a channel extending through the actuator; and a pin coupled to the lock and disposed within the cam channel, the actuator operable along a path defined by the cam and the pin to extend and retract the lock.

In Example 22, the subject matter of Example 21 optionally includes a compression member in contact with the lock and the impactor, the compression member biasing the lock to retract into the impactor.

In Example 23, the subject matter of any one or more of Examples 21-22 optionally include the actuator further comprising: a lever operable to rotate the actuator.

In Example 24, the subject matter of any one or more of Examples 21-23 optionally include the cam channel defined by: a ramp side surface biased by the compression member to engage the pin when the actuator is operated to extend the lock from the impactor.

In Example 25, the subject matter of any one or more of Examples 21-24 optionally include a torsion member internally coupled to the impactor and engageable with an internal portion of the actuator to bias the actuator to an outward position.

In Example 26, the subject matter of any one or more of Examples 21-25 optionally include the cam channel further defined by: a cam side surface opposite the ramp side surface, the cam side surface biased by the torsion member to engage the pin when the actuator is released and when the lock and impactor are secured to the implant.

In Example 27, the subject matter of any one or more of Examples 21-26 optionally include the cam side further comprising: a continually variable radiused surface in the cam side surface curved substantially away from the ramp side surface, the continually variable radiused surface engageable with the pin to restrict the lever from moving inward when the lock and the impactor are secured to the implant.

In Example 28, the subject matter of any one or more of Examples 21-27 optionally include a pivot pin connected to the impactor and extending through the actuator, the actuator rotatable about the pivot pin.

In Example 29, the subject matter of any one or more of Examples 21-28 optionally include wherein the lock further comprises a mating feature disposed proximate a distal termination of the lock, the mating feature engageable with the implant.

Example 30 is a system including the impactor tool of any of Examples 21-29, the system further comprising: a tibial tray mateable with a resected portion of a tibia.

In Example 31, the subject matter of any one or more of Examples 21-30 optionally include wherein the tibial tray further comprises a slot engageable with the mating feature to secure the tool to the tibial tray.

In Example 32, the subject matter of any one or more of Examples 21-31 optionally include a torsion pin extending through the body and configured to retain the torsion member.

In Example 33, the subject matter of any one or more of Examples 21-32 optionally include an upper compression pin securable to the lock; and a lower compression pin securable to the handle distal of the upper compression pin, the lower compression pin together with the upper compression pin retaining the compression member therebetween.

In Example 34, the subject matter of any one or more of Examples 21-33 optionally include wherein the lock further comprises a lower compression pin slot configured to receive the lower compression pin therethrough, and wherein the lower compression pin restricts translation of the lower compression pin slot to limit translation of the lock within the handle.

In Example 35, the subject matter of any one or more of Examples 21-34 optionally include wherein the mating feature of the luck further comprises a notch shaped and configured to engage and retain a portion of a tibial tray.

In Example 36, the apparatuses or method of any one or any combination of Examples 1-35 can optionally be configured such that all elements or options recited are available to use or select from.

BRIEF DESCRIPTION OF THE DRAWINGS

In the drawings, which are not necessarily drawn to scale, like numerals can describe similar components in different views. Like numerals having different letter suffixes can represent different instances of similar components. The drawings illustrate generally, by way of example, but not by way of limitation, various examples discussed in the present document.

FIG. 3 illustrates cross-sectional view of an impactor tool, in accordance with at least one example of the present disclosure.

FIGS. 4A and 4B illustrate cross-sectional views of implant assembly, in accordance with at least one example of the present disclosure.

FIGS. 5A-5D illustrate cross-sectional views of an impactor tool in various states, in accordance with at least one example of the present disclosure.

DETAILED DESCRIPTION

Knee prostheses, and in some examples, tibial trays, may require a lot of force to be inserted into the tibia of a patient. Accordingly, special tools may be required for insertion, such as an impactor and an impacting device. The present inventors propose an impactor tool including an elongate handle coupled to an impactor. The impactor can include an extending and retracting locking mechanism that is operated by an actuator including a cam. A pin of the impactor tool is movable within the cam to transfer movement of the actuator to translation of the lock. A compression spring can be included to bias the lock to a retracted position and a torsion spring can be included to bias the actuator to an outward position. In operation, a physician can operate the actuator to extend the lock and engage a tibial tray and release the actuator to secure the tray to the lock and to the impactor. The physician can then impact the impactor with an impacting device, such as a mallet, to drive the tibial tray into a desired position. Thereafter, the physician can operate the actuator to disengage the lock, removing the impactor tool from the tibial tray, so that the remainder of the arthroplasty can be performed. The details and benefits of the impactor tool and assemblies including the tool are discussed below.

As used herein, the terms "proximal" and "distal" should be given their generally understood anatomical interpretation. The term "proximal" refers to a direction generally toward the torso of a patient, and "distal" refers to the opposite direction of proximal, i.e., away from the torso of a patient. It should be understood that the use of the terms "proximal" and "distal" should be interpreted as though the patient were standing with the knee joint in extension despite the apparatuses described herein generally being used with the knee joint in flexion. The intent is to differentiate the terms "proximal" and "distal" from the terms "anterior" and "posterior". As used herein, the terms "anterior" and "posterior" should be given their generally understood anatomical interpretation. Thus, "posterior" refers to a rear of the patient, e.g., a back of the knee. Similarly, "anterior" refers to a front of the patient, e.g., a front of the knee. Thus, "posterior" refers to the opposite direction of "anterior".

Figure 1:
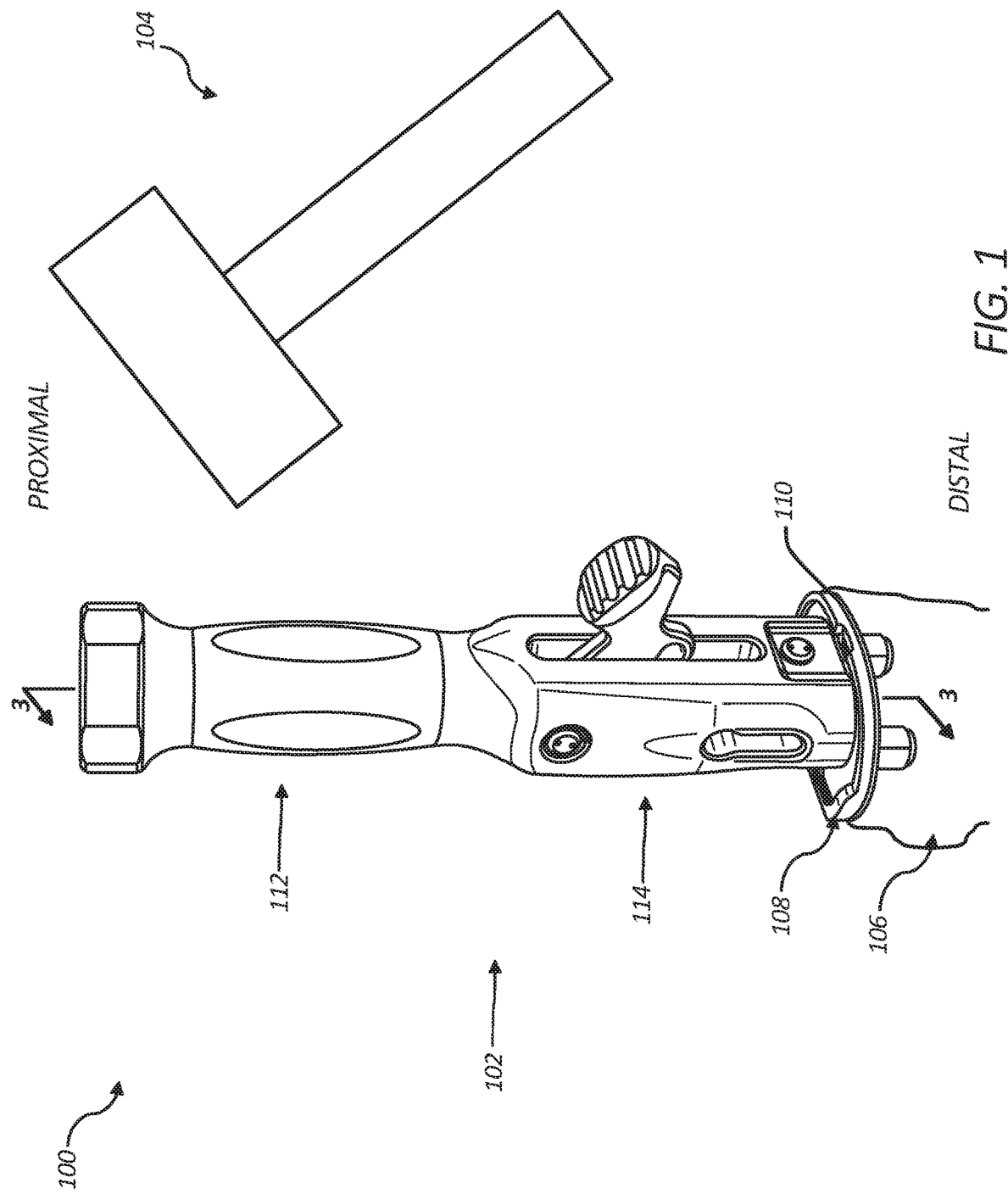
FIG. 1 illustrates an isometric view of an implant assembly, in accordance with at least one example of the present disclosure.

FIG. 1 illustrates an isometric view of an implant assembly 100, which can include impactor tool 102, impacting device 104, tibia 106, and tibial tray 108. Tibia 106 can include resected tibial portion 110. Impactor tool 102 can include handle 112 and impactor 114. Also shown in FIG. 1 are orientation indicators Proximal and Distal and arrows 3-3.

Tibia 106 can be a human tibia in need of an arthroplasty procedure. Tibia 106 can be a tibia prepared for arthroplasty, such as resected at resected tibial portion 110, to receive tibial tray 108. Tibial tray 108 can be a tibial tray configured to interface with condyles of a human femur or, in some other cases, condyle femoral implants. Tibial tray 108 can be insertable into tibia 106 at a distal portion of tibial tray 108 and a proximal portion of tibial tray 108 can be coupleable to a bearing surface that interfaces with condyles or condyle implants to provide an articulation assembly that replaces the function of a human knee.

Impactor device 104 can be a device, such as a hammer or mallet, configured to deliver a force or impulse to another object. Impactor tool 102 can be a tool configured to transfer a force from an impacting device, such as impacting device 104, to a tibial tray, such as tibial tray 108. Handle 112 can be integral to impactor tool 102 and can be connected to impactor 114. Handle 112 and impactor 114 can be comprised of lightweight materials, such as plastics or lightweight metals, such as aluminum, titanium, and the like.

Handle 112 can be configured to be grasped at handle 112 and can be configured to receive a force or impulse at a proximal end of handle 112, and transfer the force to impactor 114. Impactor 114 can be releasably coupleable to tibia tray 108, as described in detail further below.

In operation of one example, a physician can place tibia tray 108 on resected tibial portion 110, inserting a distal portion of tibia tray 108 into tibia 106. The physician can then operate impactor 104, as described further below, to couple impactor tool 102 to tibial tray 108. The physician can use impacting device 104 to apply a force or impulse to a proximal portion of handle 112, which transfers the force to impactor 114. Impactor 114 can deliver the transferred force or impulse to a tribal tray 108, causing tibial tray 108 to move into tibia 106, as desired. Once tibial tray 108 has been hammered, or forced into a desired position within and relative to tibia 106, the physician can operate impactor 114 to release impactor tool 102 from tibial tray 108 and the physician can proceed to other portions of the arthroplasty.

In some examples, impactor tool 102 can be used to transfer a force or impulse to tibia tray 108 (or another component), without coupling impactor tool 102 to tibial tray 108 (or another component). Further details of impactor tool 102 are discussed in the FIGS. below.

Figure 2:
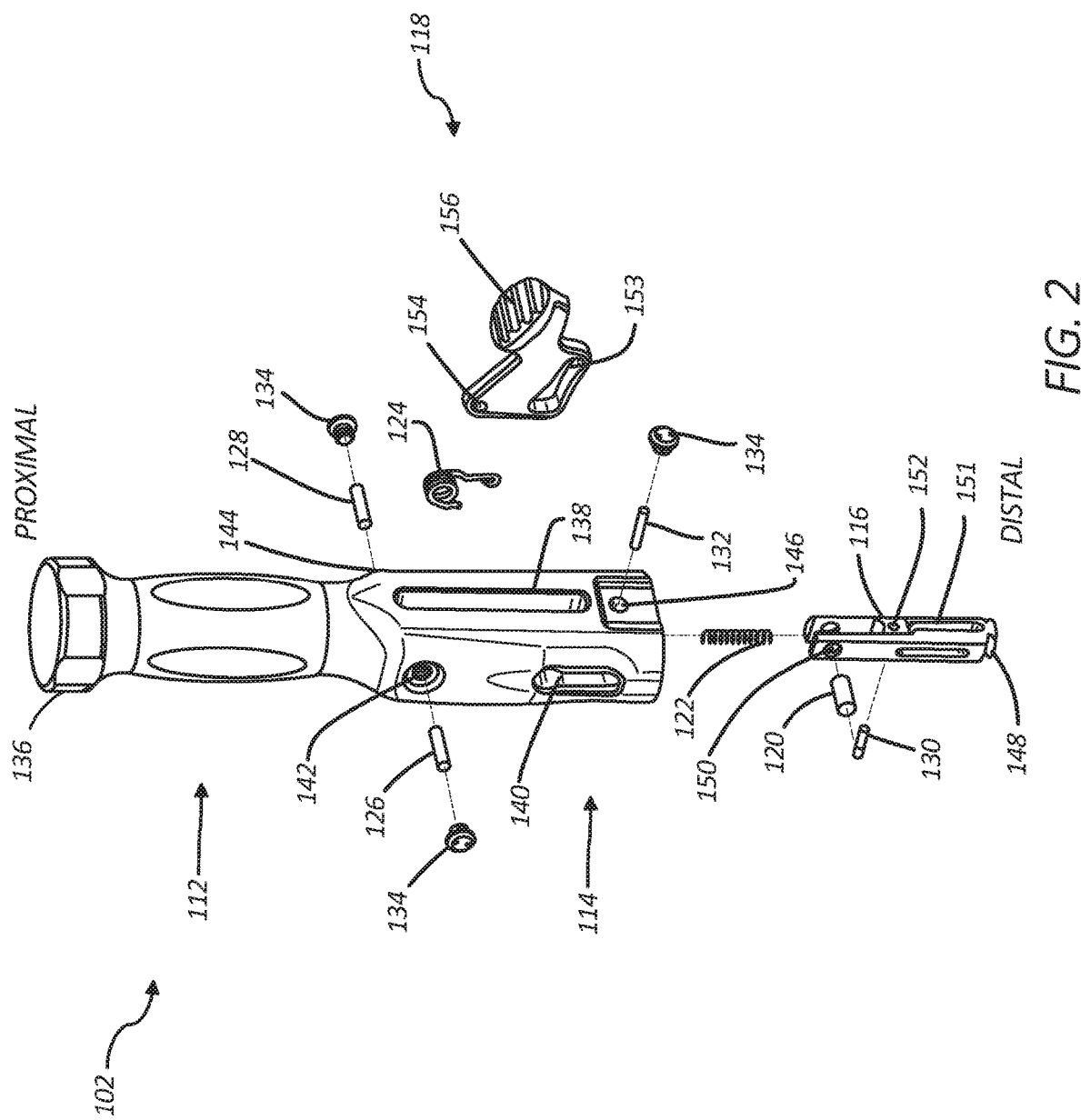
FIG. 2 illustrates an exploded isometric view of an impactor tool, in accordance with at least one example of the present disclosure.

FIG. 2 illustrates an exploded isometric view of impactor tool 102. FIG. 3 illustrates cross-sectional view of impactor tool 102 across arrows 3-3 of FIG. 1. FIGS. 2 and 3 are discussed below concurrently.

Impactor tool 102 can include handle 112 and impactor 114, as described in FIG. 1. Impactor tool 102 can also include lock 116, actuator 118, pin 120, compression member 122, torsion member 124, pivot pin 126, torsion pin 128, upper compression pin 130, lower compression pin 132, and screws 134 (shown in FIG. 2). Handle 112 can include proximal end 136. Impactor 114 can include actuator slot 138 (not visible in FIG. 3), cleaning slots 140 (only one shown in FIG. 2), pivot pin bore 142, torsion pin bore 144, and lower compression pin bores 146 (one shown in FIGS. 2 and 3). Lock 116 can include mating feature 148, pin bore 150, lower compression pin slots 151 (one shown in FIG. 2), and upper compression pin bore 152. Actuator 118 can include cam 153, pivot pin bore 154, and lever 156. Also shown in FIGS. 2 and 3 are Force F (FIG. 3 only) and orientation indicators Proximal and Distal.

Handle 112 can include proximal end 136 which can be disposed at a proximal termination of handle 136, away from impactor 114. Impactor 114 extends from handle 112 to a distal termination of impactor tool 102. Cleaning slots 140 extend through an elongate body of impactor 104 to allow access the internal components of impactor 104, such as compression member 122, for cleaning, assembly, and disassembly.

Lock 116 can be securable within impactor 114 at a proximal portion of lock 116 by pin 120. Pin 120 can be movable but limited by the surfaces or boundaries of cam 153 and movements of actuator 118. Lock 116 can be securable at a distal portion of lock 116 by lower compression pin 132. Lower compression pin 132 can be secured by lower compression pin bores 146 and by lower compression pin slots 151 of lock 116. Lower compression pin 132 can be axially secured by screw 134. Upper compression pin 130 can be secured within upper compression pin bore 152 and can be coupled only to lock 116, so that upper compression pin 130 translates or moves with lock 116. Conversely, because lower compression pin 132 can be secured to impactor 114 and passes through lower pin slots 151, lower compression pin does not move with lock 116 and stays fixed relative to impactor 114, such that lower compression pin 132 can limit translation of actuator 118 by engaging compression pin slots 151 of lock 116.

Compression member 122 can be a spring, such as a helical coil compression spring, for example. Lower compression pin 132 engages a distal portion of compression member 122 and upper compression pin 130 engages a proximal portion of compression member 122. Compression member 122 can be retained by and can be compressible between upper compression pin 130 and lower compression pin 132, which also limit translation of compression member 122 relative to lock 116, actuator 118, and impactor 114, and can prevent rotation of actuator 118 within handle 112. Mating feature 148 can be a hook, catch, or other geometric profile that is shaped to engage a portion of a tibial tray, as described further below.

Actuator 118 can couple to lock 116 internal to impactor 114 via pin 120, as described above. Cam 153 can be defined by a channel or slot extending through actuator 118 where pin 120 can be a shaft or follower that rides or follows the profile defined by the channel of actuator 118, forming cam 153. The interaction between cam 153 and pin 120 can translate rotational movement of actuator 118 into linear motion of pin 120 and therefore lock 116, as discussed in detail below.

Actuator 118 can extend from impactor 114 through actuator slot 138 such that lever 156 is external to impactor 114. Actuator 118 can also be coupled to impactor 114 at pivot pin 126, which can extend through pivot pin bore 142 of impactor 114 and through pivot pin bore 154 of actuator 118. Pivot pin 126 can be secured by fastener 134, which can be a screw, snap, and the like, permanently or releasably secured to pivot pin bore 142. When installed, actuator 118 can be pivotable or rotatable about pivot pin 126, actions which can be operated by lever 156, as described further below. Lever 156 can be sized so that it cannot pass through actuator slot 138, limiting the internal rotation of actuator 156, while the connection of cam 153 to pin 120 and lock 116 can limit the external rotation or extension of actuator 118.

Torsion member 124 can be a torsion spring, such as a torsion bar, or helical coil spring. Torsion member 124 can be disposed within impactor 114 and can be secured to impactor 114 by torsion pin 128. Torsion pin 128 can be secured within torsion pin bore 144 (shown in FIG. 3) and locked in place by fastener 134. Torsion member can engage a portion of impactor 114 and a portion of actuator 118 (as shown in FIG. 3) to bias actuator to an extended position from impactor 114 through actuator slot 138.

In operation of some examples, a physician, or any person, can apply a force F to lever 156 of actuator 118. As force F is applied to lever 156, actuator 118 can rotate about hinge pin 126 when force F is great enough to overcome a force applied to actuator 118 by torsion member 124 and when a force F is greater than the force applied to lock 116 by compression member 122. When the forces from compression member 122 and torsion member 144 are overcome by force F, actuator 118 can rotate internally, moving cam 153.

As cam 153 moves, a proximal surface of cam 153 can force pin 120 distally. Because pin 120 can be coupled to lock 116, lock 116 can translate distally as pin 120 does. As lock 116 translates distally it can extend beyond a distal termination of impactor 114, where mating feature 148 can engage a tibial tray, such as tibial tray 108 of FIG. 1. Once lock 116 has engaged the tibial tray, force F can be removed or reduced, so that the forces applied by compression member 122 and torsion member 124 cause lock 116 to move proximally, which causes pin 120 to translate proximally, and causes actuator 118 to rotate outwardly. Movement in this way can occur until the tibial tray engaged with lock 116 contacts the distal end of impactor 114. After contact, the forces of compression member 122 and torsion member 124 persist, securing the tibial tray to lock 116 and impactor 114.

Once the tibial tray is secured to impactor tool 102, impactor tool can then be used to drive the tibial tray into a tibia, as described above. Because the tibial tray can be secured to impactor tool 102, forces applied by an impacting device (such as impacting device 104 of FIG. 1) are less likely to cause impactor tool 102 to disengage from the tibial tray. Therefore, impactor tool 102 effectively transfers the force to the tibial tray while reducing the likelihood of damage to the tibial tray, tibia, or anything else. This can increase procedural efficiency, saving time and cost, and can prevent injury to the patient, providing an increased quality of life.

After the tibial tray is positioned within the tibia, as desired, actuator 118 can be operated as described above to extend lock 116 from impactor 114. While lock 116 is extended, lock 116 can be disengaged from the tibial tray, allowing impactor tool to be entirely disengaged, so that the surgical procedure may continue. Further details are discussed below. Because lock 116 can be retractable into impactor 114, impactor tool 102 can be used as an impactor without engaging lock 116 onto a tibial tray.

FIG. 4A illustrates a side cross sectional view of impactor assembly 400. FIG. 4B illustrates a front cross-sectional view of impactor assembly 400. FIGS. 4A and 4B are discussed concurrently.

Impactor assembly 400 can include impactor tool 402 and tibial tray 408. Impactor tool 402 can include handle 412, impactor 414, lock 416, actuator 418, pin 420, compression members 422A and 422B, and torsion member 424. Tibial tray 408 can include slot 460 and mating feature 462. Lock 416 can include mating feature 448. Actuator 418 can include cam 453, which can include ramp side surface 464 and cam side surface 466. Also shown in FIGS. 4A and 4B are orientation indicators Proximal, Distal, Anterior (FIG. 4A), Posterior (FIG. 4A), Medial (FIG. 4B), and Lateral (FIG. 4B).

Impactor assembly 400 can be connected and can operate similar to impactor assembly 100 of FIGS. 1-3. However, impactor assembly 400 differs in that impactor tool 402 includes compression members 422A and 422B. Each of compression members 422A and 422B can be disposed on a side of lock 416. Also, each of compression members 422A and 422B can engage internal and distally facing surface of impactor 414 and can engage pin 420.

Also, FIGS. 4A and 4B also display impactor tool 402 in a state of being locked onto tibial tray 408. In this condition, FIG. 4A shows how pin 420 engages cam side surface 466 of cam 453 when lock 416 is secured to tibial tray 408, details of which are discussed in the FIGS. below.

Also shown in the condition of FIGS. 4A and 4B are the interaction between lock 416 and tibial tray 418. Mating feature 448 can have a geometric shape that is tapered and complimentary to slot 460 of tibial tray 408, such that mating feature 448 can slide anteriorly to posteriorly into slot 460 and then mating feature 448 cannot be displaced proximally, distally, medially, or laterally from tibial tray 408. Then, if lock 416 is slid further backward, mating feature 448 of lock 416 can engage mating feature 462 of tibial tray 408. In some examples, mating feature 448 of lock 416 and mating feature 462 of tibial tray 408 can have complementary shapes, such as a hook, ledge, shelf, or catch, preventing proximal movement of impactor tool 402 relative to tibial tray 408 when mating feature 448 engages mating feature 462. Then, when lock 416 is engaged with mating feature 462 of tibial tray 408 and when lock 416 is retracted into impactor 414, anterior wall 468 can prevent impactor tool 402 from moving anteriorly relative to tibial tray 408. In this state, impactor tool 402 cannot move in any direction relative to tibial tray 408 without operating actuator 418 to extend lock 416 from impactor 414. This locking mechanism therefore provides the benefit of a secure lock between impactor tool 402 and tibial tray 408 in every direction.

FIG. 5A illustrates impactor tool 502 in a retracted state. FIG. 5B illustrates impactor tool 502 in a partially retracted state. FIG. 5C illustrates impactor tool 502 in a partially extended state. FIG. 5D illustrates impactor tool 502 in an extended state. FIGS. 5A-5D are discussed concurrently.

Impactor tool 502 can include impactor 514, lock 516, actuator 518, and pin 520. Actuator 518 can include cam 523, which can include ramp side surface 564 and cam side surface 566. Also shown in FIGS. 5A-5D is force F and orientation indicators Proximal and Distal.

Impactor tool 502 can be connected and can operate similar to impactor tool 102 of FIGS. 1-3 and impactor 402 of FIG. 4. FIGS. 5A-5D show impactor tool in operational stages.

As shown in FIG. 5A, when lock 516 is in a fully retracted position, pin 520 rests in the proximal-most portion of cam 523 along ramp side surface 564. As force F is applied to actuator 518, ramp side surface 564 of cam 523 applies a force to pin 520, causing pin 520 and lock 516 to move distally, as shown in FIG. 5B. Pin 520 maintains contact with ramp side surface 564 due to proximal force applied by compression members (such as compression members 422A and 422B of FIG. 4). If force F is maintained, actuator 518 will continue to rotate generally distally and inward, causing ramp side surface 564 to force pin 520 further distally and lock 516 further distally, extending lock 516 from impactor 514. Extension of lock 516 can continue until pin 520 contacts a termination of cam 523 where ramp side surface 564 and cam side surface 566 meet, as shown in FIG. 5D. When force F is removed from actuator 518, actuator 518 can rotate generally outward and proximally and pin 520 can move along ramp side surface moving generally proximally and allowing lock 516 to retract.

Figure 6D:
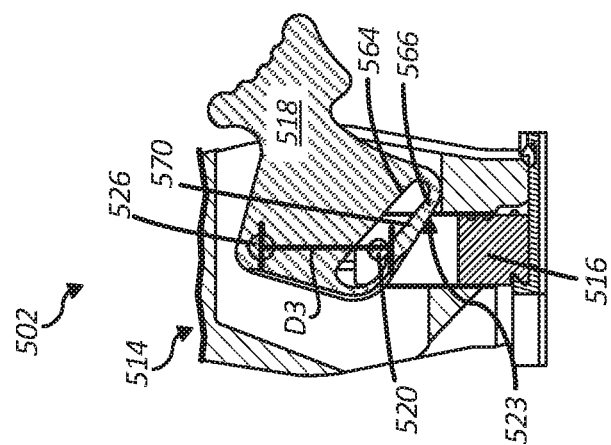
FIGS. 6A-6D illustrate cross-sectional views of an impactor tool in various states, in accordance with at least one example of the present disclosure.
Figure 6C:
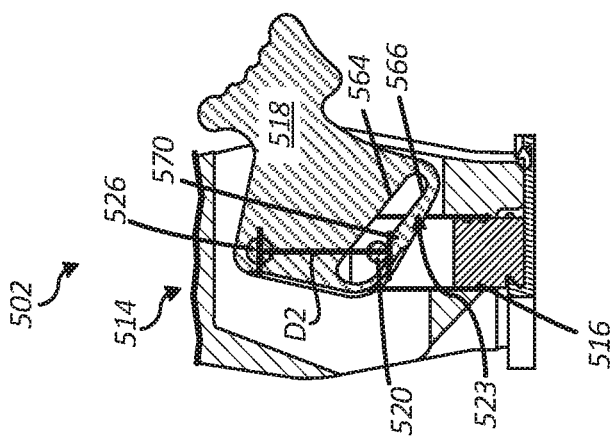
Figure 6B:
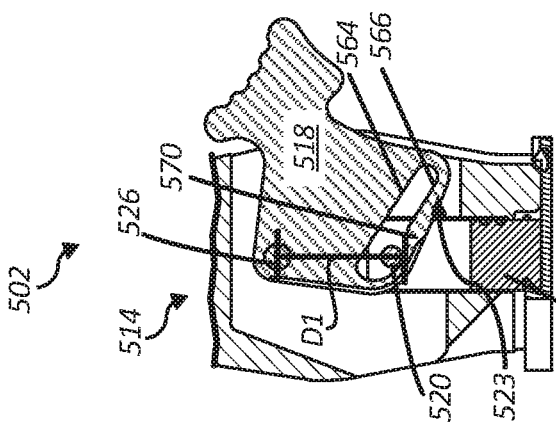
Figure 6A:
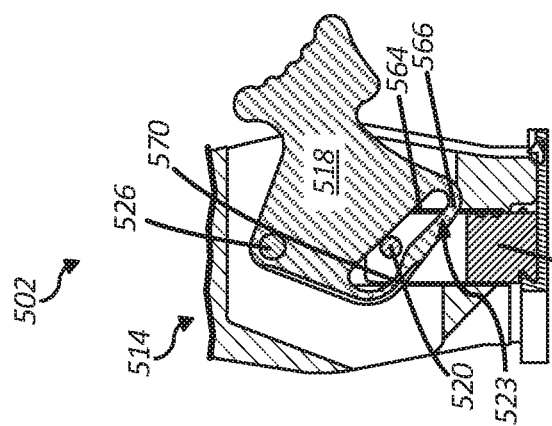
Figure 7:
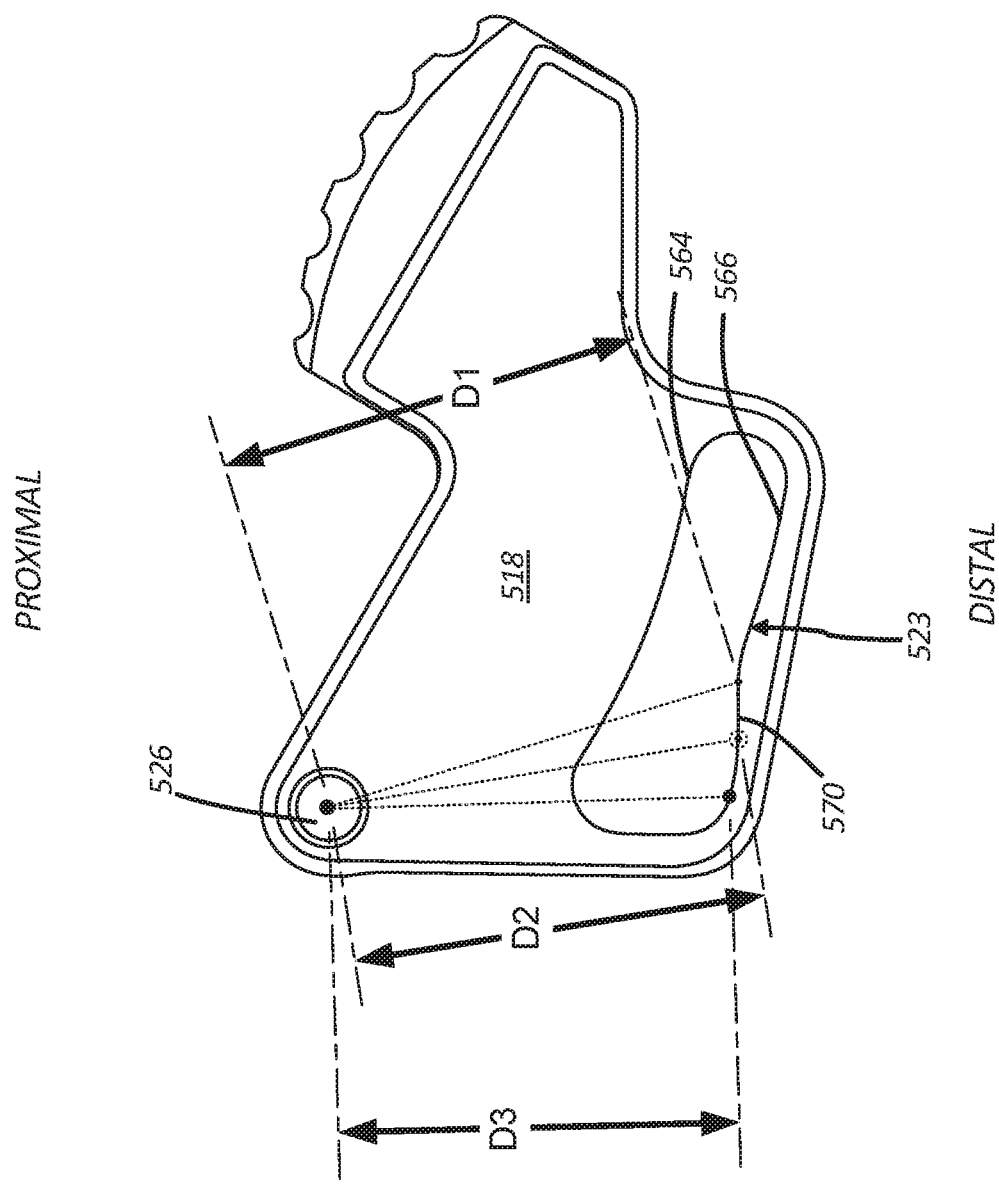
FIG. 7 illustrates a side view of an actuator of an impactor tool, in accordance with at least one example of the present disclosure.

FIG. 6A illustrates impactor tool 502 with lock 516 in a retracted state and actuator 518 in an unlocked position. FIG. 6B illustrates impactor tool 502 with lock 516 in a retracted position and with actuator in a locked position with positive manufacturing tolerances. FIG. 6C illustrates impactor tool 502 with lock 516 in a retracted position and with actuator in a locked position with no manufacturing tolerances. FIG. 6B illustrates impactor tool 502 with lock 516 in a retracted position and with actuator in a locked position with negative manufacturing tolerances. FIG. 7 illustrates a side view actuator 518 showing distances D1, D2, and D3. FIGS. 6A-6D and 7 are discussed below concurrently.

Impactor tool 502 can include impactor 514, lock 516, actuator 518, pin 520, and pivot pin 526. Actuator 518 can include cam 523, which can include ramp side surface 564 and cam side surface 566. Cam side surface 566 can include continually variable radiused surface 570. Also shown in FIGS. 6A-6D and 7 are distance D1, distance D2, distance D3, and orientation indicators Proximal and Distal.

As shown in FIG. 6A, lock 516 is in a retracted state and actuator 518 is in an unlocked position. When actuator 518 is released, lock 516 is then free to retract until lock 516 engages a mating feature of a tibial tray (such as mating feature 462 of tibial tray 408 of FIGS. 4A-4D) and the tibial tray comes into contact with impactor 514. At that point, a torsion member (such as torsion member 424 of FIGS. 4A and 4B) can cause actuator 518 to move outwardly and can cause pin 520 to engage cam side surface 566. Pin 520 can engage a continually variable radiused surface 570, which can be a portion of cam side surface 566 of cam 523 curved generally away from ramp side surface 564. This contact can result in a locking action between lock 516, impactor 514, and the tibial tray. In this way, impactor tool 502 is easily operated to lock onto a tibial tray.

Because cam side surface 566 and a continually variable radiused surface 570 offer several distance between cam side surface 566 of cam 523 and pivot pin 526, contact between pin 520 and cam side surface 566 allows a variable locking distance between pivot pin 526 and pin 520. For example, when manufacturing tolerances create or tolerance stack creates a positive manufacturing tolerance offset, as shown in FIG. 6B, the locking distance will be distance D1. When there is no manufacturing tolerance offset, as shown in FIG. 6C, the locking distance will be distance D2. When manufacturing tolerances or tolerance stack creates a negative manufacturing tolerance offset, as shown in FIG. 6D, the locking distance will be distance D3, where distance D1 is greater than distance D2 is greater than distance D3.

In the prior art, some locked-on impactors have used other methods to account for this adjustment for manufacturing tolerances, such as a threaded connection that uses a screw driver to adjust for tolerances, which can be a time-consuming process. The present disclosure addresses this problem by including continually variable radiused surface 570.

In each tolerance case (distance D1, distance D2, and distance D3) actuator 518 is locked in place by cam side surface 566 and continually variable radiused surface 570, despite the variance in locking distance. In this way, the locking mechanism of impactor tool 502 is self-adjusting to account for manufacturing tolerances, which can save time in set-up of tool 502 or during a procedure. Also, because impactor tool 502 properly functions throughout a range of manufacturing tolerances, the present design offers the benefit of increased usability of manufacturing yield, which can save time and cost. Further, it allows impactor tool 502 to be used with implants having mating feature size variability. That is, the mating feature on a small implant may not require the same clamping or locking distance as the mating feature on a larger implant.

Figure 8:
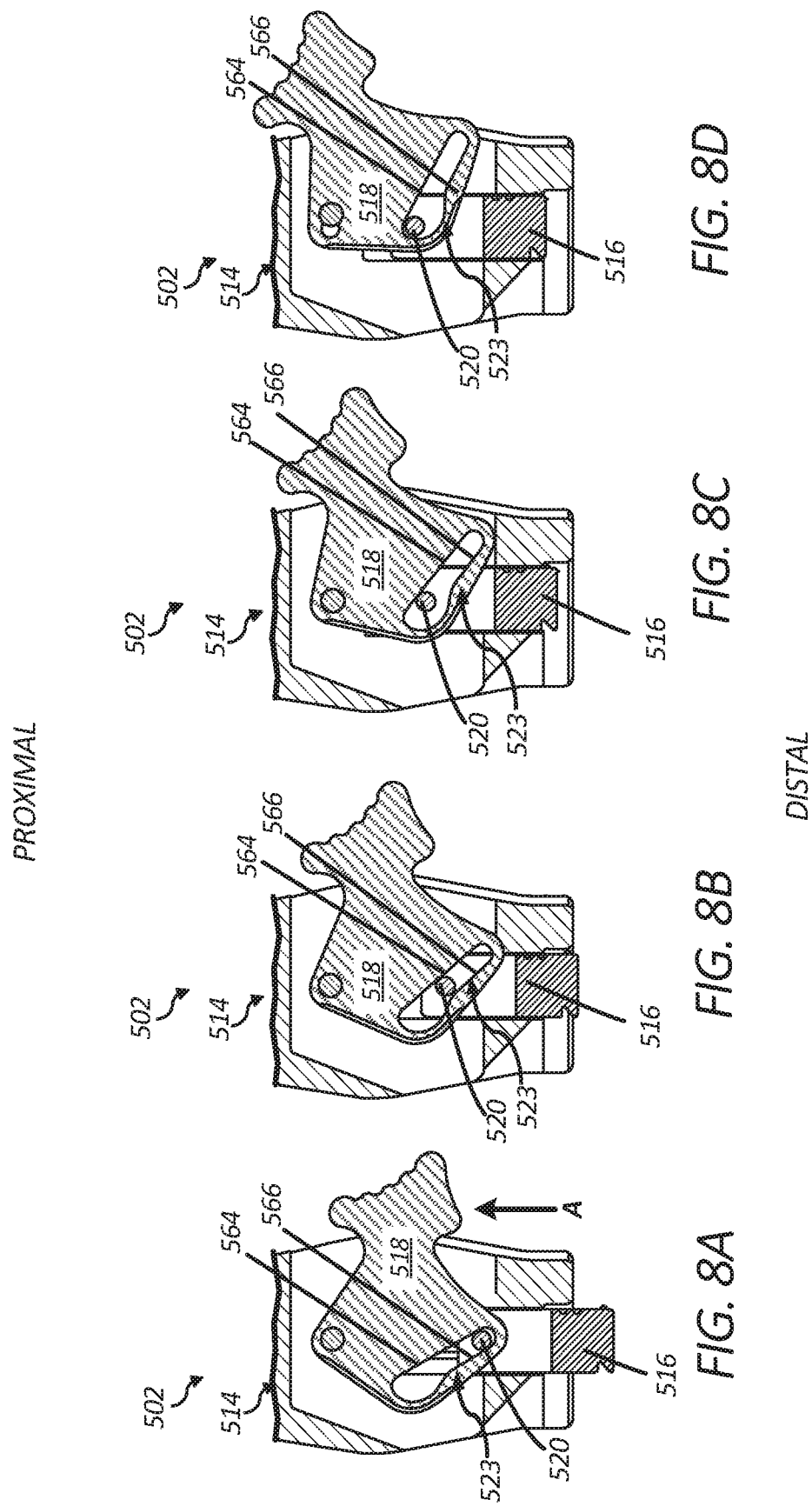
FIGS. 8A-8D illustrate cross-sectional views of an impactor tool in various states, in accordance with at least one example of the present disclosure.

FIG. 8A illustrates impactor tool 502 in an extended state. FIG. 8B illustrates impactor tool 502 in a partially extended state. FIG. 8C illustrates impactor tool 502 in a partially retracted state. FIG. 8D illustrates impactor tool 502 in a retracted state. FIGS. 8A-8D are discussed concurrently.

Impactor tool 502 can include impactor 514, lock 516, actuator 518, and pin 520. Actuator 518 can include cam 523, which can include ramp side surface 564 and cam side surface 566. Also shown in FIGS. 8A-8D is direction A and orientation indicators Proximal and Distal.

Impactor tool 502 can be connected and can operate as described above in FIGS. 5A-6D. FIGS. 8A-8D further show how lock 516 can be retracted into impactor 514.

As shown in FIG. 8A, when lock 516 is in a fully extended position, pin 520 rests in the distal-most portion of cam 523 where ramp side surface 564 meets cam side surface 566. When actuator 518 is released, a torsion device (such as torsion device 424 of FIGS. 4A and 4B) causes actuator 518 to rotate about a pivot pin 526, generally proximally, in direction A. When this occurs, compression members (such as compression members 422A and 422B of FIGS. 4A and 4B) force pin 520 to move proximally to contact ramp side surface 564 of cam 523, as shown in FIG. 8B, allowing lock 516 to retract into impactor 514. As actuator 518 continues to move proximally, pin 520 continues to ride along ramp side surface 564, as shown in FIG. 8C, allowing lock 516 to retract further inwards. Retraction can occur until pin 520 contacts the proximal-most portion of cam 523, as shown in FIG. 8D, where cam side surface 566 meets ramp side surface 564. Impactor tool 502 offers the benefit of disengaging the tibial tray without applying a large force or torque. This can allow a physician to quickly and easily engage and disengage a tibial tray with impactor tool 502.

Figure 9:
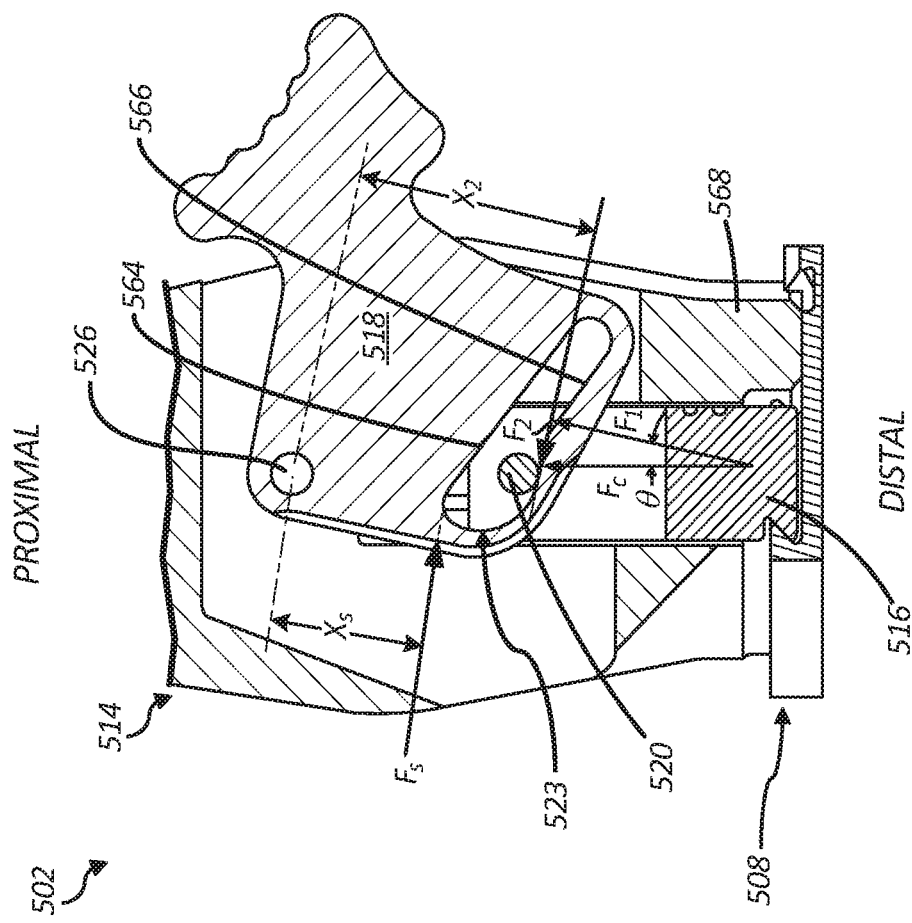
FIG. 9 illustrates a cross-sectional view of a portion of an impactor tool, in accordance with at least one example of the present disclosure.

FIG. 9 illustrates a cross-sectional view impactor tool 502, which can include impactor 514, lock 516, actuator 518, and pin 520. Actuator 518 can include cam 523, which can include ramp side surface 564 and cam side surface 566. Also shown in FIG. 9 are spring force Fs, clamping force (or compression) Fc, compression component forces $F_1$ and $F_2$, component force angle $\theta$, distances $X_1$ and $X_2$, and orientation indicators Proximal and Distal.

The components shown in FIG. 9 can be connected and can operate consistently with the components of FIGS. 4-8D. FIG. 9 further shows how a small spring force Fs creates a relatively large clamping force Fc.

Force Fs will create a moment about pivot pin 526, which can be balanced by the clamping or compression force Fc, specifically, by component force $F_2$. The moments created by these forces can be balanced about pivot pin 526 as shown below in equations 1 and 2 below $$Fs * Xs = F_2 * X_2 \qquad \text{Equation 1}$$

Solving for $F_2$ in Equation 2 gives:

$$F_2 = (Fs * Xs)/X_2 \qquad \text{Equation 2}$$

The reaction force $F_2$ can be a component of the clamping force Fc, where the other component is $F_1$, as shown in Equation 3 below.

$$\sin \theta = F_2/Fc \qquad \text{Equation 3}$$

Force $F_2$ as given in Equation 2 can be substituted into Equation 3 as shown below in Equation 4.

$$\sin \theta = (Fs * Xs)/(Fc * X_2) \qquad \text{Equation 4}$$

Equation 4 can be rearranged in Equation 5 as:

$$Fc = (Fs/\sin \theta) * (Xs/X_2) \qquad \text{Equation 5}$$

In some examples, such as those shown in the embodiments above, a small angle $\theta$, such as 10° or smaller, can provide a relatively large clamping force. For example, an angle $\theta$ of 5° can provide:

$$Fc = (Fs/0.087) * (Xs/X_2) \qquad \text{Equation 6}$$

Simplifying Equation 6 can provide:

$$Fc = (Fs * 11.47) * (Xs/X_2) \qquad \text{Equation 7}$$

That is, clamping force Fc can be approximately ten times spring force Fs when angle $\theta$ is 50. Accordingly, impactor tool 502 can apply a large clamping force Fc to retain tibial tray 508 to impactor 514.

Additional Notes

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) can be used in combination with each other. Other examples can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above detailed description, various features can be grouped together to streamline the disclosure. This should not be interpreted as intending that an unclaimed disclosed feature is essential to any claim. Rather, inventive subject matter can lie in less than all features of a particular disclosed example. Thus, the following claims are hereby incorporated into the detailed description as examples or embodiments, with each claim standing on its own as a separate example, and it is contemplated that such examples can be combined with each other in various combinations or permutations. The scope of the invention should be determined with reference to the appended claims, along with the full scope of equivalents to which such claims are entitled.

The invention claimed is:

1. An impactor tool comprising:
   a handle;
   an impactor coupled to the handle;
   a lock extendable from the impactor to engage an implant and retractable into the impactor to secure the lock and the impactor to the implant;
   an actuator protruding from the impactor and coupled to the lock, the actuator comprising:
      a cam defined by a channel extending through the actuator; and
      a pin coupled to the lock and disposed within the cam channel, the actuator operable along a path defined by the cam and the pin to extend the lock from the impactor and to retract the lock entirely into the impactor.

2. The impactor tool of claim 1, further comprising:
   a compression member in contact with the lock and the impactor, the compression member biasing the lock to retract into the impactor.

3. The impactor tool of claim 2, the actuator further comprising:
   a lever operable to rotate the actuator.

4. The impactor tool of claim 3, the cam channel defined by:
   a ramp side surface biased by the compression member to engage the pin when the actuator is operated to extend the lock from the impactor.

5. The impactor tool of claim 4, further comprising:
   a torsion member internally coupled to the impactor and engageable with an internal portion of the actuator to bias the actuator to an outward position.

6. The impactor tool of claim 5, the cam channel further defined by:
   a cam side surface opposite the ramp side surface, the cam side surface biased by the torsion member to engage the pin when the actuator is released and when the lock and impactor are secured to the implant.

7. The impactor tool of claim 6, the cam side further comprising:
   a continually variable radiused surface in the cam side surface curved substantially away from the ramp side surface, the continually variable radiused surface engageable with the pin to restrict the lever from moving inward when the lock and the impactor are secured to the implant.

8. The impactor tool of claim 1, further comprising:
   a pivot pin connected to the impactor and extending through the actuator, the actuator rotatable about the pivot pin.

9. The impactor tool of claim 1, further comprising:
   a mating feature disposed proximate a distal termination of the lock, the mating feature engageable with the implant.

10. A tibial implant impactor assembly comprising:
    a tibial tray mateable with a resected portion of a tibia;
    an implant impactor tool comprising:
       a handle;
       an impactor connected to the handle and engageable with the tibial implant; and
       a lock extendable from the impactor to engage an implant and retractable into the impactor to secure the lock and the impactor to the tibial tray;
       an actuator protruding from the impactor and coupled to the lock, the actuator comprising:
          a cam defined by a channel extending through the actuator; and
          a pin coupled to the lock and disposed within the cam channel, the actuator operable along a path defined by the cam and the pin to extend the lock from the impactor and to retract the lock into the impactor.

11. The assembly of claim 10, further comprising:
    a mating feature disposed proximate a distal termination of the lock, the mating feature engageable with the implant.

12. The assembly of claim 11, the tibial tray further comprising:
    a slot engageable with the mating feature to secure the tool to the tibial tray.

13. The assembly of claim 10 further comprising:
    a compression member in contact with the lock and the impactor, the compression member biasing the lock to retract into the impactor.

14. The assembly of claim 13, further comprising:
    a torsion member internally coupled to the impactor and engageable with an internal portion of the actuator to bias the actuator to an outward position.

15. The assembly of claim 14, the cam defined by:
    a ramp side surface biased by the compression member to engage the pin when the actuator is operated to extend the lock from the impactor.

16. The assembly of claim 15, the cam further defined by:
a cam side surface opposite the ramp side surface, the cam side surface biased by the torsion member to engage the pin when the actuator is released and when the lock and impactor are secured to the implant.

17. The assembly of claim 16, further comprising:
a continually variable radiused surface in the cam side surface curved substantially away from the ramp side surface, the a continually variable radiused surface engageable with the pin to restrict the lever from moving inward when the lock and the impactor are secured to the implant.

\* \* \* \* \*

UNITED STATES PATENT AND TRADEMARK OFFICE
CERTIFICATE OF CORRECTION

PATENT NO. : 10,888,436 B2
APPLICATION NO. : 15/880975
DATED : January 12, 2021
INVENTOR(S) : Dykema et al.

Page 1 of 1

It is certified that error appears in the above-identified patent and that said Letters Patent is hereby corrected as shown below:

In the Claims

In Column 15, Line 9, in Claim 17, after "the", delete "a"

Signed and Sealed this
Thirtieth Day of March, 2021

Drew Hirshfeld
*Performing the Functions and Duties of the*
*Under Secretary of Commerce for Intellectual Property and*
*Director of the United States Patent and Trademark Office*